United States Patent
Huang

(10) Patent No.: US 6,399,028 B1
(45) Date of Patent: Jun. 4, 2002

(54) IGNITABLE BEEHIVE TYPE WICK END IN AN AROMATIC OIL LAMP AND THE ATTACHMENT FOR INSTANTANEOUSLY ENHANCING THE DENSITY OF THE ESSENCE OIL

(76) Inventor: Shu-Li Huang, P.O. Box No. 6-57, Chung-Ho, Taipei 235 (TW)

( * ) Notice: Subject to any disclaimer, the term of this patent is extended or adjusted under 35 U.S.C. 154(b) by 0 days.

(21) Appl. No.: 09/986,492
(22) Filed: Nov. 9, 2001
(51) Int. Cl.⁷ ................................. A62B 7/08
(52) U.S. Cl. .................. 422/125; 422/125; 422/1; 422/5; 431/320; 239/44
(58) Field of Search ............... 431/320; 422/1, 422/5, 122, 125; 239/44

(56) References Cited

U.S. PATENT DOCUMENTS 5,840,246 A * 11/1998 Hammons et al. ............. 422/4
5,840,257 A * 11/1998 Bureau et al. ............. 422/125

FOREIGN PATENT DOCUMENTS

FR 2762895 A1 * 11/1998

* cited by examiner

*Primary Examiner*—Robert J. Warden, Sr.
*Assistant Examiner*—Sean E. Conley

(57) ABSTRACT

An ignitable beehive type wick end in an aromatic oil lamp and the attachment for instantaneously enhancing the density of the essence oil, wherein the ceramic wick end includes at least a hollow mushroom structure composed by a bracket seat as well as an upper cover and both are clamped by a clip ring, is characterized that at least a beehive type air conducting block is disposed inside the wick end for conducting the current therein to lower the temperature; a supporting stand disposed with a placement frame covers the upper aspect of a bottle body; a ceramic block with a recessed groove on the top portion and impregnated with the essence oil is placed on the placement frame; the heat heated, raised upwards and dispersed from the ceramic wick end vaporizes the essence oil thereon to instantaneously enhance the density of the essence oil in the air.

7 Claims, 6 Drawing Sheets

IGNITABLE BEEHIVE TYPE WICK END IN AN AROMATIC OIL LAMP AND THE ATTACHMENT FOR INSTANTANEOUSLY ENHANCING THE DENSITY OF THE ESSENCE OIL

BACKGROUND OF THE INVENTION

1. Field of the Invention

The present invention relates to an ignitable beehive type wick end in an aromatic oil lamp and the attachment for instantaneously enhancing the density of the essence oil, more particularly to a structure comprising at least a porous air conducting block inside the wick end; the burning wick end generates a current course, increases convention rate as well as evens the heat dissipation and the burning; furthermore, a supporting stand with a ceramic block is disposed in the upper aspect of the wick end of an essence oil bottle; that the heating simultaneously heats the said ceramic block with additional essence oil being dropped thereon to further fast enhance the volatizing function of the essence oil is the feature of the present invention.

2. Description of the Prior Art

Accordingly, the aromatic oil is a substance which can disperse efficient constituent; the volatized gas dispersed indoors not only smells fragrant, but also has the herbal therapeutic effect; once breathed in, it can comfort and relax the human body physically and emotionally; since most of the aromatic oils are applied for maintaining and recuperating one's health, the number of users is increasing.

Wherein, the aromatic oil lamp has to use special kind of burner, referring to FIG. 6; the aromatic oil is impregnated into a bottle and a string of wick (81) elevates the oil upwards, wherein the upper aspect of the wick (81) is encased with a disk seat (80) and a wick end main body (90) is further assembled thereon; the said wick end main body (90) is made of ceramic material and is approximately formed as a mushroom body with an opening hole disposed in the lower aspect thereof; the central portion extends to form an air chamber (91) and the end of the wick (81) is forced therein; the said wick (81) absorbs the oil inside the bottle all the way up to the air chamber (91) and the wick end main body (90) is ignited to volatilize the oil molecule inside the air chamber (91) for burning.

However, since there is no any special structure inside the air chamber (91), the wick (81) smoldering inside sometimes overheats to not only damage the essence oil, but also to fail to burn completely and that accelerates the generation of burned black greasy dirt (92); the most disadvantage of the prior art device is that those residuum in coarse grains will gradually block the air holes inside the air chamber (91) and make the permeation of the oily gas insufficient and unable to be ignited.

Furthermore, when the essence oil is just ignited, the temperature is not very high and the diffusion effect of the fragrance is very limited; more especially, it takes a while for obtaining the fragrant waft instead of filling the indoor in time; therefore, another shortcoming of the prior art device is that the user might waste a lot of time in waiting for the slow dispersion of the essence oil; the additional shortcoming of the prior art device is that during the initial burning, the heat tends to loose and that causes undesired effect of burning and dispersion of the waft of the essence oil.

SUMMARY OF THE INVENTION

Therefore, the primary objective of the present invention is to address and improve the undesirable temperature during the initial application of the prior art device and the overheating problems during the after application by forming the wick end as a hollow mushroom structure comprising a bracket seat as well as an upper cover and both are clamped by a clip ring; a beehive type air conducting block is disposed inside to make the burning oily gas, conducting by the beehive type air conducting block, capable of not only reducing the burning temperature, but also increasing the convention rate, evening the heat dissipation and enhancing the aromatic effect.

Another objective of the present invention is to dispose a supporting stand in the upper aspect of the wick end, a placement frame on the said support stand and a ceramic block on the placement frame; thereby, the dispersed heat under the absorption of the said ceramic block and proper reflection back to the wick end makes the heat inbetween gradually condense and accelerate the burning of the essence oil to achieve more efficient and complete diffusion of the fragrance indoors.

Yet another objective of the present invention is to especially dispose a recessed slot on the top portion of the said ceramic block for receiving proper amount of essence oil, becoming an area for volatilizing essence oil as well as for instantaneously twice enhancing the diffusion rate of the density of the waft of the essence oil in the air and that is the feature of the present invention.

For achieving the above objectives, the brief description of the drawings below is followed by the detailed description of the preferred embodiment.

DETAILED DESCRIPTION OF THE PREFERRED EMBODIMENTS

Figure 1:
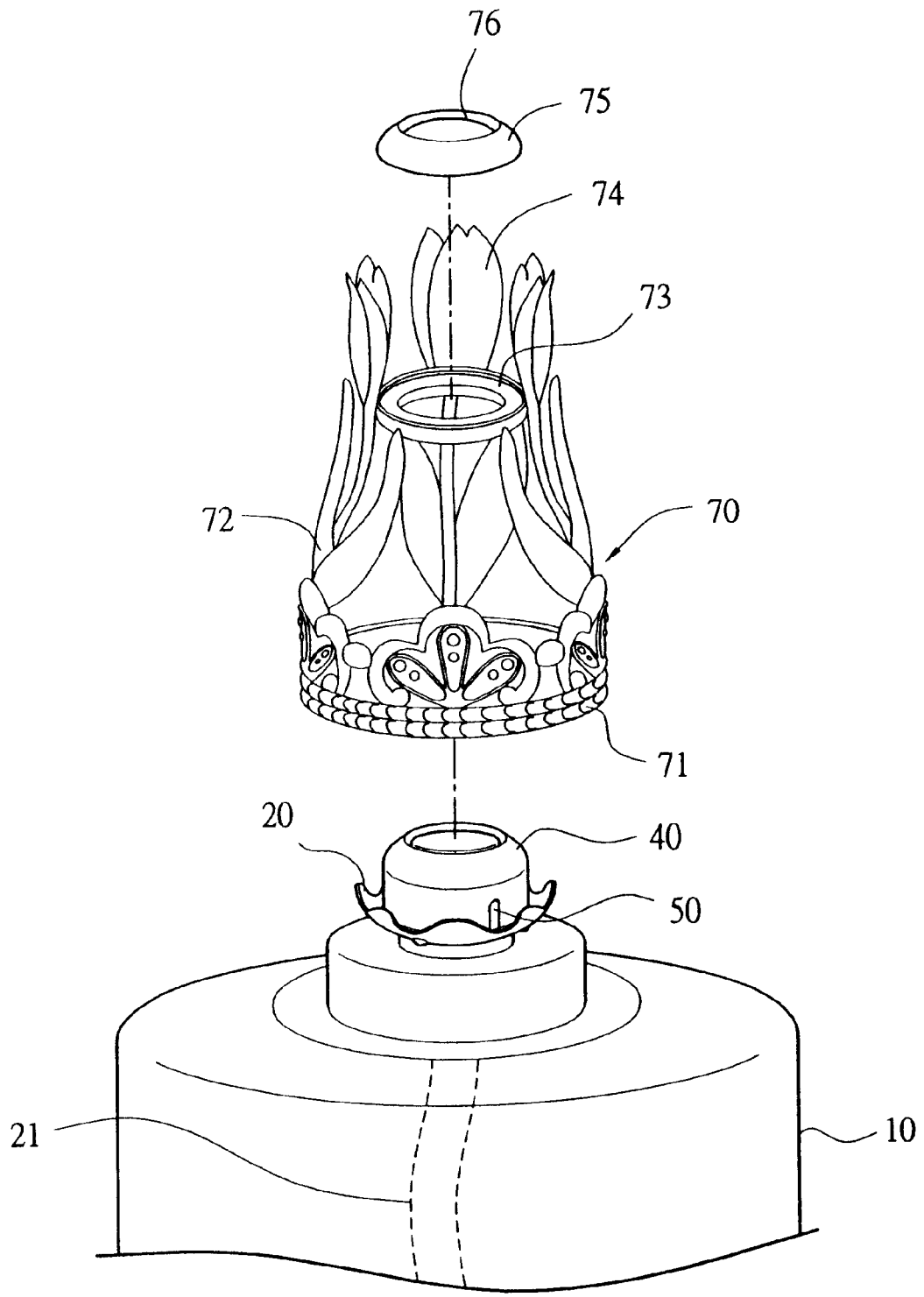
FIG. 1 is an exploded drawing of the partial structure of the present invention.
Figure 2:
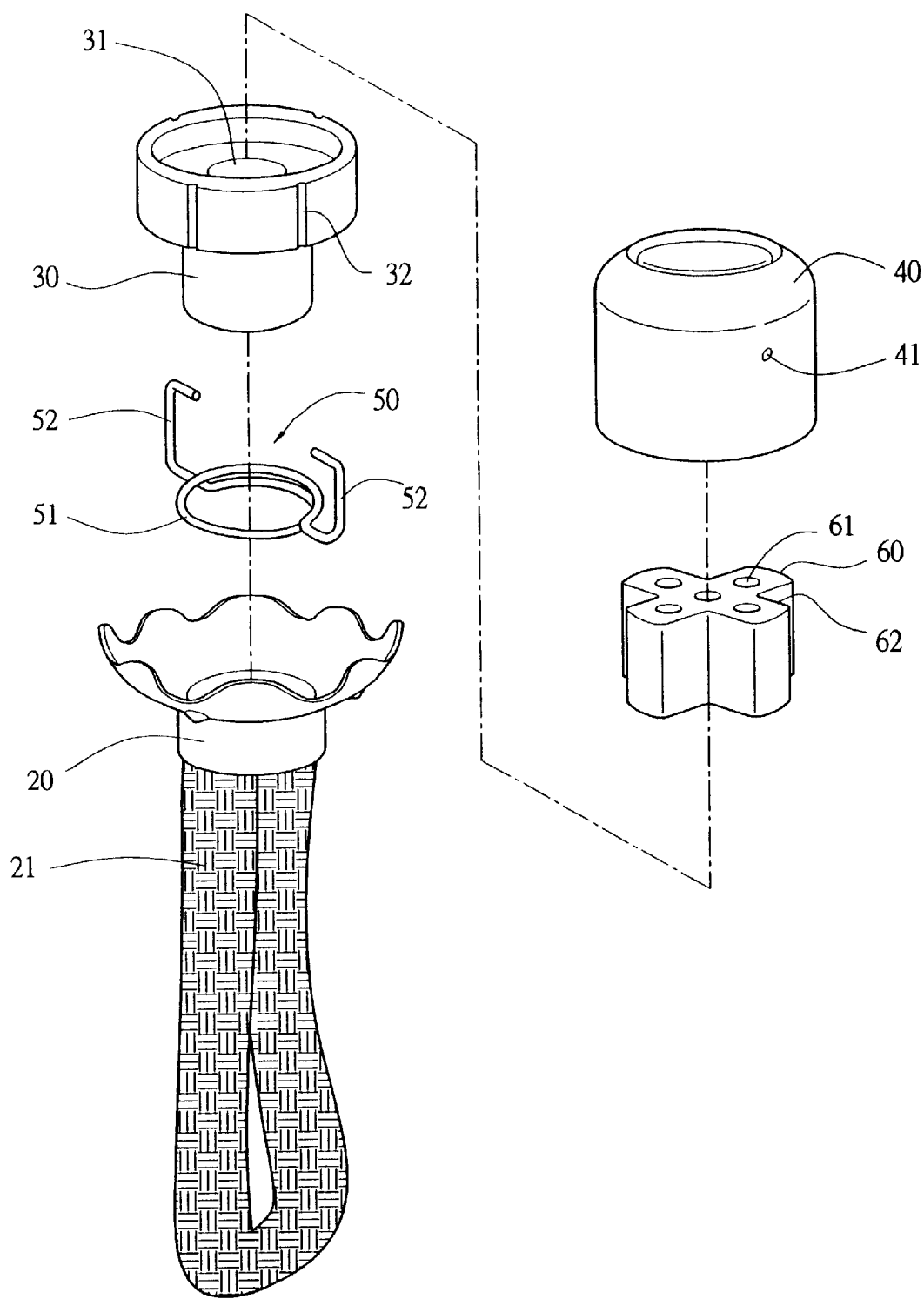
FIG. 2 is an exploded drawing of the wick end structure of the present invention.

One of the exemplary embodiments of the present invention, referring to FIGS. 1 and 2, mainly comprises a wick (21) disposed at the opening of the bottle (10), a disk seat (20) encased at the upper end of the wick (21) and a wick end structure on the disk seat (20) to connect with the wick (21); the said wick end structure comprises a bracket seat (30), an upper cover (40), an air conducting block (60) and a clip ring (50), wherein the bracket seat (30) is a columnar body with a through hole (31) in the center and the peripheral side in the upper aspect thereof projecting outwards to form a disk body with a plurality of recessed longitudinal grooves (32) disposed on the peripheral side; the upper cover (40) is in the form of an arch to be fitted with the top portion of the bracket seat (30) and retaining holes (41) are disposed on two sides thereof.

The ceramic air conducting block (60) is approximately in a columnar form with a plurality of recessed longitudinal and arcurate grooves (62) disposed on the outer wall to form petaline cutting planes; furthermore, a plurality of longitudinal through holes (61) are disposed along the axial direction of the air conducting block (60) to make the disk body as a beehive type structure.

The clip ring (50) is a metal wire in a proper length with the center coiled into a plurality of rings of spring structure (51) and two ends thereof extend to form C-shaped retaining ends (52).

At least one air conducting block (60) is placed in the through hole (31) of the bracket seat (30) and the upper cover (40) is fitted with the bracket seat (30); the clip ring (50) in a spring structure (51) is encased upwards from the columnar body in the lower aspect of the bracket seat (30) and the retaining ends (52) on two sides are pulled outwards; at this time, the spring structure (51) in the center tightly is fastened to the bracket seat (30) and the retaining ends (52) clip into the retaining holes (41) on two sides of the upper cover (40), thereby the upper cover (40) and the bracket seat (30) are firmly fastened by the clip ring (50).

Figure 3:
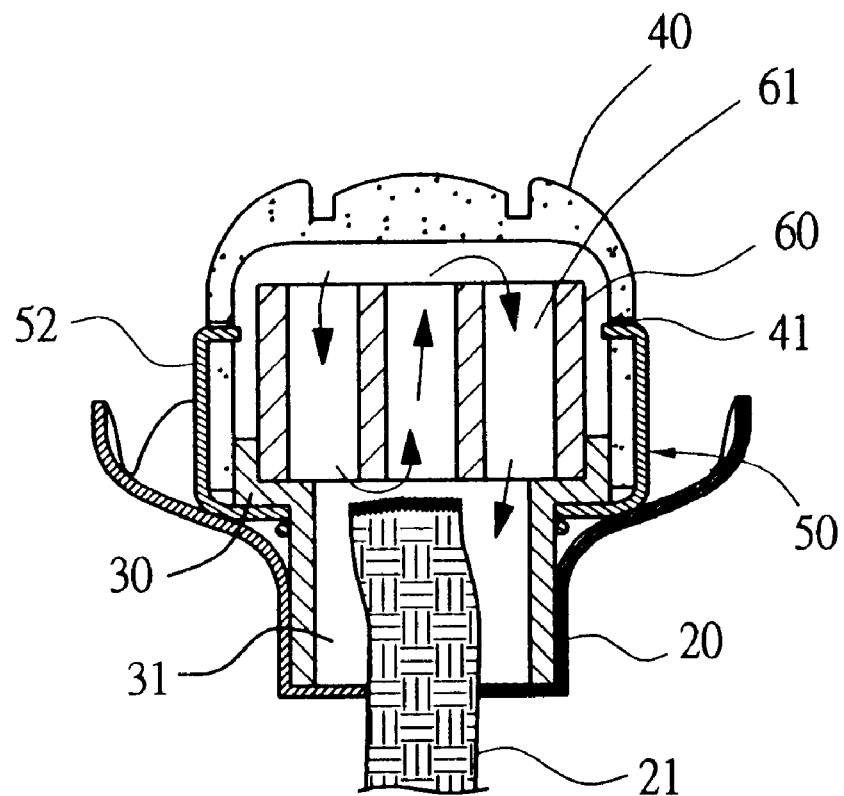
FIG. 3 is a cross-sectional and structural drawing of the wick end of the present invention.

Referring to FIGS. 2 and 3, the wick (21) inside the bottle absorbs the essence oil to the inside of the wick end; after being ignited, the oily gas permeates the arcurate planes between the insides of the through hole (31) of the bracket seat (30) and the upper cover (40); being conducted by the beehive type air conducting block (60), the burning temperature thereof is lowered and the burning hot air flows upwards through the inside and outside conduction of the through holes (61) as well as the recessed arcurate grooves (62) to increase the convection rate and even the heat dissipation, therefore, the burning is more complete; even after a long term of using, the end of the wick of the oil lamp can be disassembled by dismounting the clip ring (50) to disconnect the bracket seat (30) and the upper cover (40) for individual cleansing to completely get rid of the greasy dirt for reusing and that is the advantage and the feature of the present invention.

Furthermore, being disposed with a plurality of longitudinal grooves (32) on the peripheral side, the bracket seat (30), fitly encased with the upper cover (40) or not, conducts the current in a smoother action and that is another advantage of the present invention.

Figure 4:
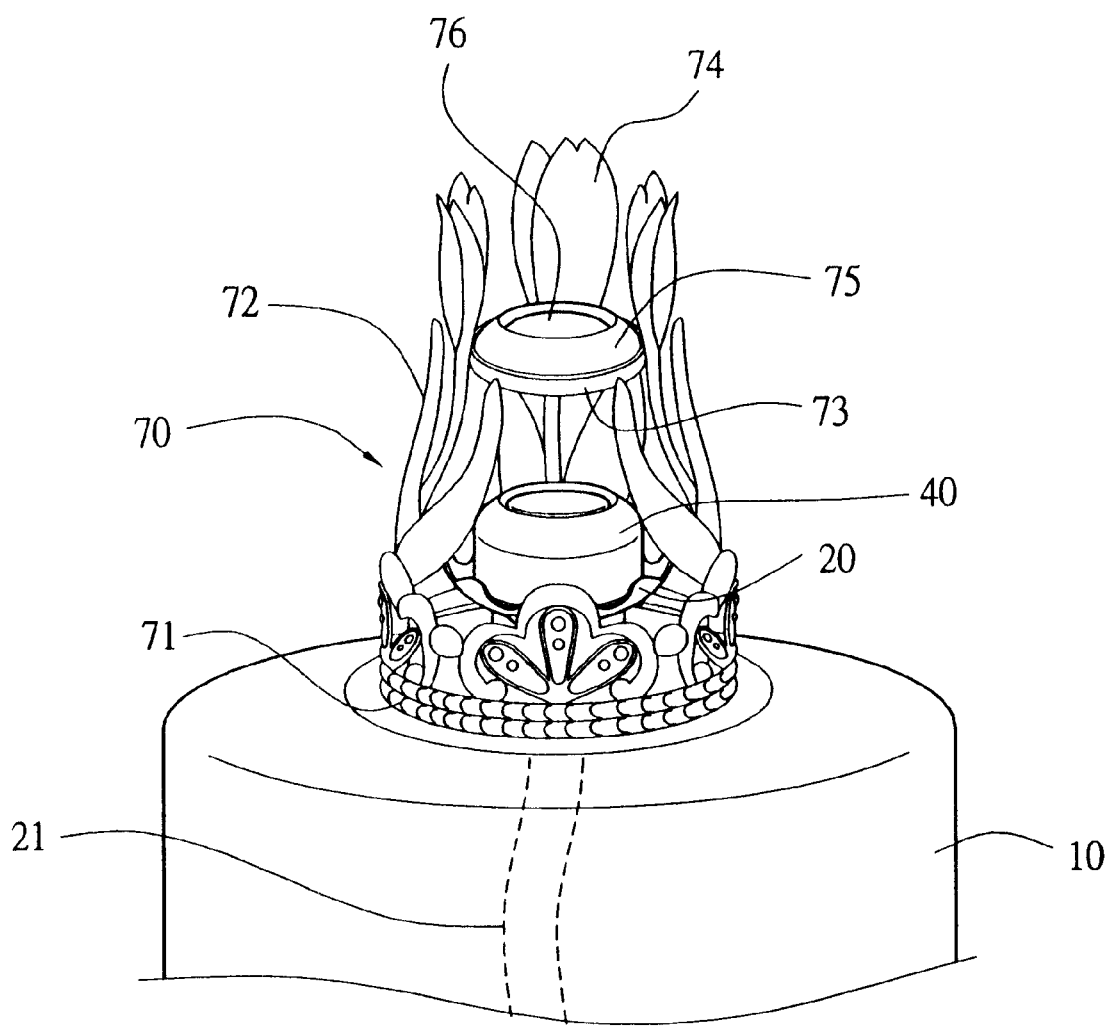
FIG. 4 is an external drawing of the application of the supporting stand of the present invention.

Yet another feature of the present invention, referring to FIGS. 1 and 4, is to dispose a supporting stand (70) in the upper aspect of the opening of the bottle (10); the said supporting stand (70) has a annular seat (71) disposed at the bottom portion to be placed on the peripheral side of the disk seat (20) in the upper aspect of the bottle (10), the annular seat (71) extends upwards to form a supporting post (72) in a certain height; the upper aspect of the supporting post (72) is disposed with an annular placement frame (73) with a plurality of stop portions (74) mounted on the peripheral side thereof.

Figure 5:
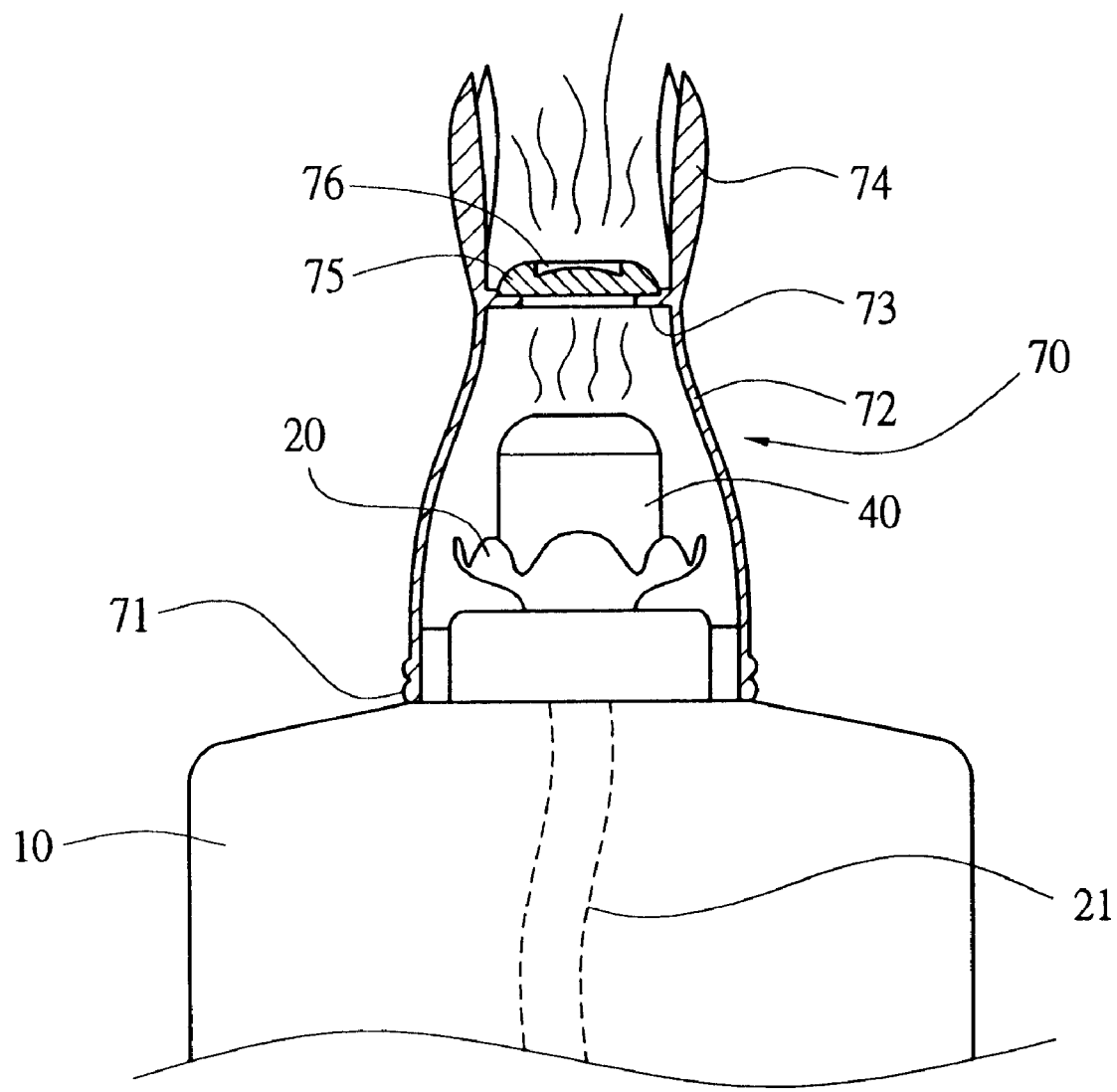
FIG. 5 is a cross-section al drawing of the relative position between the supporting stand and the wick end of the present invention.
Figure 6:
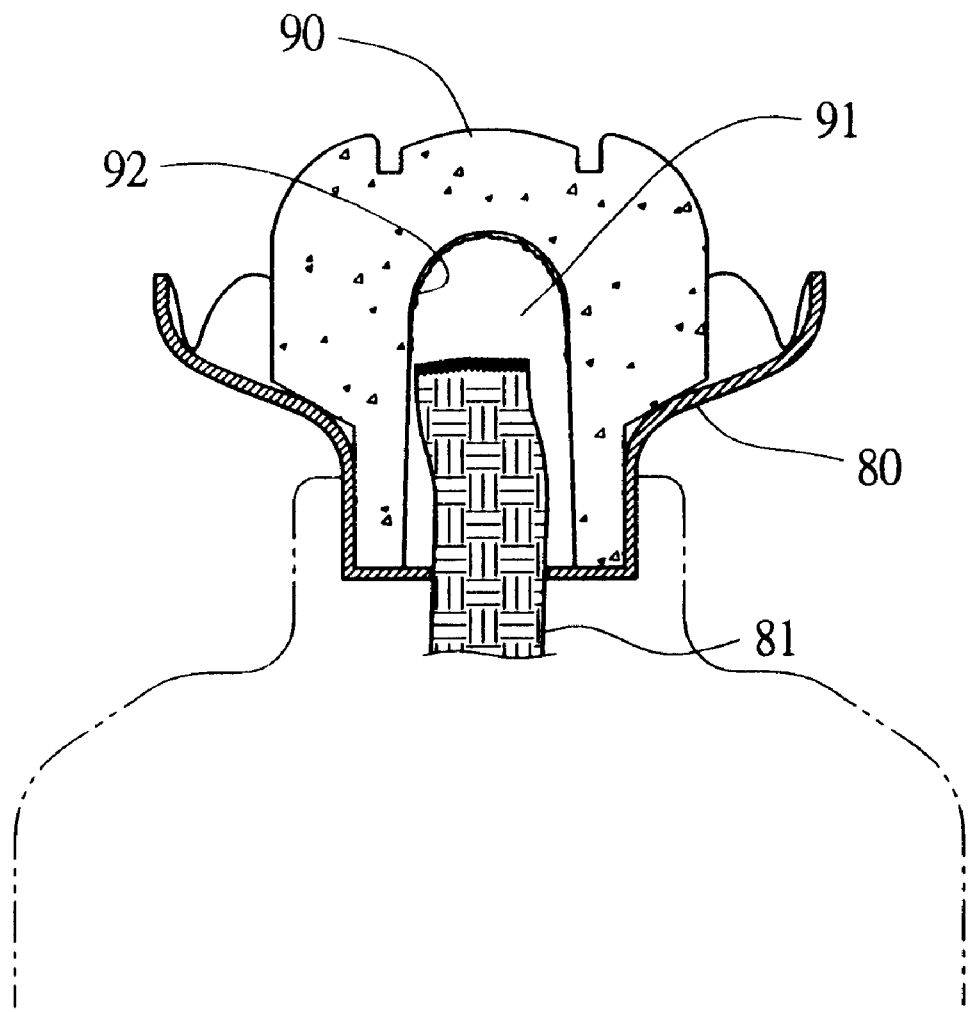
FIG. 6 is a structural and cross-sectional drawing of the prior art wick end.

A ceramic block (75) in a certain thickness has a recessed slot (76); referring to FIGS. 1 and 5, the said ceramic block (75) can be placed on the placement frame (73) of the supporting stand (70) while the stop portions (74) fitly hold the ceramic block (75); the heat dispersed from the ceramic wick end rises upwards and heats the ceramic block (75), thereby the heat inbetween gathers and is not subject to diffuse; furthermore, several drops of essence oil can be dripped into the recessed slot (76) of the ceramic block (75) to make that area have the volatizable essence oil for obtaining stronger aromatic waft and increasing the diffusion rate; that is another feature of the present invention.

Since the present invention has a special idea to design the air conducting block capable of not only lowering the internal burning temperature to avoid the damage to the essence oil and to save the amount of it to be used, but also achieving the efficiency of evening the heat dissipation, increasing the air convention rate and easy dismounting and dirt cleansing.

Furthermore, by disposing a ceramic block in the upper aspect of the wick end, the supporting stand of the present invention has the effect of gathering the heat during the initial burning and instantaneously enhancing the burning temperature in time to obtain better volatizing efficiency; in addition, the top portion of the ceramic block is disposed with a recessed slot holding a proper amount of essence oil as an area for dispersing the essence oil, therefore, during the initial burning, the volatizing efficiency of the essence oil is instantaneously enhanced to obtain more fragrant waft and increase twice the diffusion rate without wasting time; that is another advantage of the present invention.

It is of course to be understood that the embodiment described herein is merely illustrative of the principles of the invention and that a wide variety of modifications thereto may be effected by persons skilled in the art without departing from the spirit and scope of the invention as set forth in the following claims.

What is claimed is:

1. An ignitable beehive type wick end in an aromatic oil lamp and the attachment for instantaneously enhancing the density of the essence oil mainly comprises a disk seat at the upper end of the wick disposed in a essence oil bottle; the disk seat is mounted with a ceramic wick end structure comprising at least a bracket seat and an upper cover to form a hollow air chamber of a mushroom structure and both are clamped by a clip ring; the present invention is characterized that:

a supporting stand in a certain height is disposed in the upper aspect of the said bottle;

at least one ceramic air conducting block is disposed inside the said hollow air chamber, the said air conducting block is approximately in the form of a columnar body with a plurality of longitudinal through holes disposed along the axial direction thereof to form the entire body as a beehive type structure thereby to lower the burning temperature, increase the convention rate and even the heat dissipation.

2. An ignitable beehive type wick end in an aromatic oil lamp and the attachment for instantaneously enhancing the density of the essence oil according to claim 1, wherein the outer wall of the columnar body of the air conducting block is also disposed with a plurality of recessed longitudinal and arcurate grooves to form petaline cutting planes.

3. An ignitable beehive type wick end in an aromatic oil lamp and the attachment for instantaneously enhancing the density of the essence oil according to claim 1, wherein two sides of the upper cover are disposed with retaining holes; the clip ring is a metal wire with the center coiled into a plurality of rings of spring structure and two ends thereof extend to form C-shaped retaining ends; the said clip ring is inserted upwards from the lower aspect of the bracket seat by the spring structure while the retaining ends on two sides retain into the retaining holes on two sides of the upper cover to make the upper cover and the bracket seat be firmly fastened by the clip ring.

4. An ignitable beehive type wick end in an aromatic oil lamp and the attachment for instantaneously enhancing the density of the essence oil according to claim 1, wherein a plurality of longitudinal grooves are disposed on the peripheral side of the bracket seat to make the current conducting action herefrom smoother no matter if the bracket seat is fitly encased with the upper cover or not.

5. An ignitable beehive type wick end in an aromatic oil lamp and the attachment for instantaneously enhancing the density of the essence oil according to claim 1, wherein the bottom portion of the supporting stand is fixed on the bottle and a placement frame is disposed on the top portion thereof;

a ceramic block in a proper thickness and dripped with several drops of essence oil is place on the placement frame of the supporting stand to be heated by the heat dispersed from the wick end and rose upwards to instantaneously enhance the volatizing rate and the density of the essence oil.

6. An ignitable beehive type wick end in an aromatic oil lamp and the attachment for instantaneously enhancing the density of the essence oil according to claim 5, wherein the top portion of the ceramic block is disposed with a recessed slot for receiving the essence oil.

7. An ignitable beehive type wick end in an aromatic oil lamp and the attachment for instantaneously enhancing the density of the essence oil according to claim 5, wherein one of the structures of the supporting stand has an annular seat disposed on the bottom portion thereof; it can be placed on the peripheral side of the disk seat in the upper aspect of the bottle; the annular seat extends upwards to dispose a supporting post in a certain height and an annular placement frame is disposed in the upper aspect of the supporting post; a plurality of stop portions are disposed on the peripheral side of the placement frame.

* * * * *